United States Patent
Makimizu et al.

(10) Patent No.: US 8,221,900 B2
(45) Date of Patent: Jul. 17, 2012

(54) ZINC-BASED METAL PLATED STEEL SHEET

(75) Inventors: Yoichi Makimizu, Tokyo (JP); Sakae Fujita, Tokyo (JP); Naoto Yoshimi, Tokyo (JP); Masahiko Tada, Tokyo (JP); Shinji Ootsuka, Tokyo (JP); Hiroyuki Masuoka, Tokyo (JP); Katsuya Hoshino, Tokyo (JP); Hiroshi Kajiyama, Tokyo (JP); Masayasu Nagoshi, Tokyo (JP); Wataru Tanimoto, Tokyo (JP); Kyoko Fujimoto, Tokyo (JP)

(73) Assignee: JFE Steel Corporation (JP)

( * ) Notice: Subject to any disclaimer, the term of this patent is extended or adjusted under 35 U.S.C. 154(b) by 36 days.

(21) Appl. No.: 12/675,851

(22) PCT Filed: Sep. 3, 2008

(86) PCT No.: PCT/JP2008/066276
§ 371 (c)(1),
(2), (4) Date: Mar. 1, 2010

(87) PCT Pub. No.: WO2009/031699
PCT Pub. Date: Mar. 12, 2009

(65) Prior Publication Data
US 2010/0255341 A1    Oct. 7, 2010

(30) Foreign Application Priority Data
Sep. 4, 2007  (JP) ................. 2007-228517

(51) Int. Cl.
*B32B 15/18*  (2006.01)
*B32B 15/04*  (2006.01)

(52) U.S. Cl. ........ 428/659; 428/632; 428/657; 428/658; 205/141

(58) Field of Classification Search .......... None
See application file for complete search history.

(56) References Cited

U.S. PATENT DOCUMENTS

| | | | |
|---|---|---|---|
| 4,226,645 A * | 10/1980 | Waid et al. | 148/547 |
| 4,242,400 A * | 12/1980 | Smith et al. | 428/201 |
| 4,244,998 A * | 1/1981 | Smith | 428/195.1 |
| 4,261,965 A * | 4/1981 | Fukuda et al. | 423/544 |
| 4,734,536 A * | 3/1988 | Nagahara et al. | 585/269 |
| 5,641,578 A * | 6/1997 | Yoshimi et al. | 428/623 |
| 6,495,788 B1 * | 12/2002 | Chiriotti et al. | 219/69.12 |
| 6,528,182 B1 * | 3/2003 | Bello et al. | 428/628 |
| 7,291,402 B2 * | 11/2007 | Kazuhisa et al. | 428/626 |
| 2003/0003322 A1 * | 1/2003 | Yamamoto et al. | 428/659 |
| 2003/0089201 A1 * | 5/2003 | Harlamovs et al. | 75/722 |
| 2004/0258849 A1 * | 12/2004 | Boyd | 427/433 |
| 2005/0066773 A1 * | 3/2005 | Harlamovs et al. | 75/721 |
| 2005/0126338 A1 * | 6/2005 | Yadav | 75/255 |
| 2007/0193413 A9 * | 8/2007 | Harlamovs et al. | 75/721 |
| 2008/0308192 A1 | 12/2008 | Bello et al. | |

FOREIGN PATENT DOCUMENTS

| | | |
|---|---|---|
| JP | 53-060332 A | 5/1978 |
| JP | 53-60332 A | 5/1978 |
| JP | 1-319661 A | 12/1989 |
| JP | 2-190483 A | 7/1990 |
| JP | 3-191093 A | 8/1991 |
| JP | 4-088196 A | 3/1992 |
| JP | 2003-306781 A | 10/2003 |
| JP | 2007-517135 A | 6/2007 |
| JP | 2010-202960 | * 9/2010 |

OTHER PUBLICATIONS

Philip Schweitzer Corrosion of Linings and Coatings, 2006, p. 437-438.*
Panchenko et al . Protection of Metals, 37, N4, 2001, pp. 367-384.*
Ramanauskas et al. 3rd Latin American Region Corrosion Congress, 1998, pp. 1-9.*
Ramanauskas et al. Corrosion Science 40, N2/3, 1998, pp. 401-410.*
Quintana et al. JCPDS—International Centre for Diffraction Data 1997, pp. 1-9.*
Muster et al. Corrosion Science 46, 2004, 2319-2335.*
P. Schweitzer. Corrosion of Linings and Coatings. CPC Press, 2006 pp. 437-446.*

* cited by examiner

*Primary Examiner* — Jennifer McNeil
*Assistant Examiner* — Vera Katz
(74) *Attorney, Agent, or Firm* — DLA Piper LLP (US)

(57) ABSTRACT

A zinc-based metal plated steel sheet is excellent in tribological properties during press forming. An oxide layer containing crystalline $3Zn(OH)_2 \cdot ZnSO_4 \cdot xH_2O$ is formed on a plated surface. The oxide layer has a thickness of 10 nm or more. The crystalline oxide layer is composed of $3Zn(OH)_2 \cdot ZnSO_4 \cdot 3\text{-}5H_2O$.

4 Claims, 2 Drawing Sheets

SLIDING DIRECTION OF SAMPLE

SLIDING DIRECTION OF SAMPLE ered steel sheet # ZINC-BASED METAL PLATED STEEL SHEET

RELATED APPLICATIONS

This is a §371 of International Application No. PCT/JP2008/066276, with an international filing date of Sep. 3, 2008 (WO 2009/031699 A1, published Mar. 12, 2009), which is based on Japanese Patent Application Nos. 2007-228517, filed Sep. 4, 2007, and 2008-181082, filed Jul. 11, 2008, the subject matter of which is incorporated by reference.

TECHNICAL FIELD

This disclosure relates to a zinc-based metal plated steel sheet excellent in tribological property during press forming.

BACKGROUND

Zinc-based metal plated steel sheets are widely used in many fields, in particular, for automobile bodies. When used for automobile bodies, they are subjected to press forming before use. Zinc-based metal plated steel sheets, however, have the disadvantage that their press formability is inferior to that of cold-rolled steel sheets. This is because in a press die, the friction resistance of a surface-treated steel sheet is larger than that of a cold-rolled steel sheet. That is, the surface-treated steel sheet does not smoothly flow into the die at a portion of the surface-treated steel sheet having a large friction resistance to the die and a bead. This is liable to cause rupture of the steel sheet.

In recent years, the demand for high-tensile steel sheets has increased to reduce the weight of automobile bodies. High-tensile steel sheets have press formability inferior to that of mild steel sheets. Thus, high-tensile steel sheets are easily ruptured at portions of high-tensile steel sheets having a large friction resistance to dies and beads.

Galvannealed steel sheets are excellent in weldability and paintability compared with galvanized steel sheets and, thus, more preferably used for automobile bodies.

A galvannealed steel sheet is produced as follows: a steel sheet is subjected to galvanizing and then heat treatment. As a result, an alloying reaction in which Fe in the steel sheet and Zn in a plating layer are diffused occurs, thereby forming a Fe—Zn alloy phase. The Fe—Zn alloy phase is in the form of a layer usually including a $\Gamma$ phase, $\delta_1$ phase, and a $\xi$ phase. Hardness and a melting point tend to decrease as the Fe concentration decreases, i.e., in a sequence of the $\Gamma$ phase→the $\delta_1$ phase→the $\xi$ phase. Thus, a high-hardness, high-melting point film with high Fe concentration is effective from the viewpoint of achieving good tribological properties because adhesion does not easily occur. Galvannealed steel sheets with the emphasis on press formability are produced in such a manner that average Fe concentrations in films are relatively high.

In a film with high Fe concentration, however, hard and brittle $\Gamma$ phase is readily formed at the interface between the plating film and the steel sheet. Peeling from a surface boundary, i.e., powdering, is disadvantageously liable to occur during processing. Thus, as shown in Japanese Unexamined Patent Application Publication No. 1-319661, for the purpose of striking a balance between tribological properties and anti-powdering properties, a method for forming a hard Fe-based alloy layer as a second layer serving as an upper layer is employed. Disadvantageously, production by the method is costly.

As another method for improving press formability of a zinc-based metal plated steel sheet, a method for applying high-viscosity lubricant oil is widely used. In this method, however, a defect of coating due to a defect of degreasing occurs in an application step because of high viscosity of the lubricant oil. Furthermore, the lack of oil during press forming disadvantageously causes unstable press performance and other problems. Thus, improvement in the press formability of galvannealed steel sheets is strongly required.

As a method to overcome the foregoing problems, Japanese Unexamined Patent Application Publication Nos. 53-60332 and 2-190483 each disclose a technique for improving weldability or processability by subjecting surfaces of a zinc-based metal plated steel sheet to electrolytic treatment, immersion treatment, coating and oxidation treatment, or heat treatment to form an oxide film mainly composed of ZnO.

Japanese Unexamined Patent 4-88196 discloses a technique for improving press formability and chemical conversion treatability by immersing surfaces of a zinc-based metal plated steel sheet in an aqueous solution containing 5 to 60 g/L sodium phosphate and having a pH of 2 to 6, electrolytic treatment, or applying the solution described above to form an oxide film mainly composed of a P oxide.

Japanese Unexamined Patent Application Publication No. 3-191093 discloses a technique for improving press formability and chemical conversion treatability by subjecting surfaces of a zinc-based metal plated steel sheet to electrolytic treatment, immersion treatment, coating, coating and oxidation treatment, or heat treatment to form a Ni oxide.

Japanese Unexamined Patent Application Publication No. 2003-306781 discloses a technique for improving tribological properties by bringing a galvannealed steel sheet into contact with an acidic solution to form an oxide mainly composed of Zn on surfaces of the steel sheet and suppress adhesion between a plating layer and a press die.

The technique for improving press formability by forming an oxide mainly composed of Zn on surfaces of steel sheet disclosed in Japanese Unexamined Patent Application Publication No. 2003-306781 and the like has the advantage over the technique using Ni and the like disclosed in Japanese Unexamined Patent Application Publication No. 3-191093 in production cost and environmental loading because Zn contained in the plated steel sheet is mainly used. In the case where the steel sheet is used for a difficult-to-form component, however, a high degree of press formability is required, so that further improvement in tribological property may be required.

It could therefore be helpful to provide a zinc-based metal plated steel sheet excellent in tribological properties during press forming compared with the technique for improving press formability by forming an oxide mainly composed of Zn on surfaces of a steel sheet.

SUMMARY

We conducted studies on tribological properties of a galvannealed steel sheet and found the following:

A flat portion on a surface of the galvannealed steel sheet is present as a projection compared with a surrounding portion. The flat portion mainly comes into actual contact with a press die during press forming. Thus, the presence of an oxide layer containing crystalline 3Zn(OH)$_2$·ZnSO$_4$·3-5H$_2$O in the flat portion prevents adhesion between a plating layer and the die. In addition to the galvannealed steel sheet, also for a hot-dip galvanized steel sheet and an electrogalvanized steel sheet that are not subjected to allying treatment, the presence of an oxide layer containing crystalline 3Zn(OH)$_2$·

$ZnSO_4 \cdot 3\text{-}5H_2O$ on a plated surface prevents adhesion between a plating layer and the die.

We thus provide:

(1) A zinc-based metal plated steel sheet includes an oxide layer containing crystalline $3Zn(OH)_2 \cdot ZnSO_4 \cdot xH_2O$, in which the oxide layer is formed on a plated surface, and the oxide layer has a thickness of 10 nm or more.

(2) In the zinc-based metal plated steel sheet described in item (1), the crystalline oxide layer is composed of $3Zn(OH)_2 \cdot ZnSO_4 \cdot 3\text{-}5H_2O$.

The zinc-based metal plated steel sheet has a low friction resistance and stably provides excellent press formability.

Figure 1:
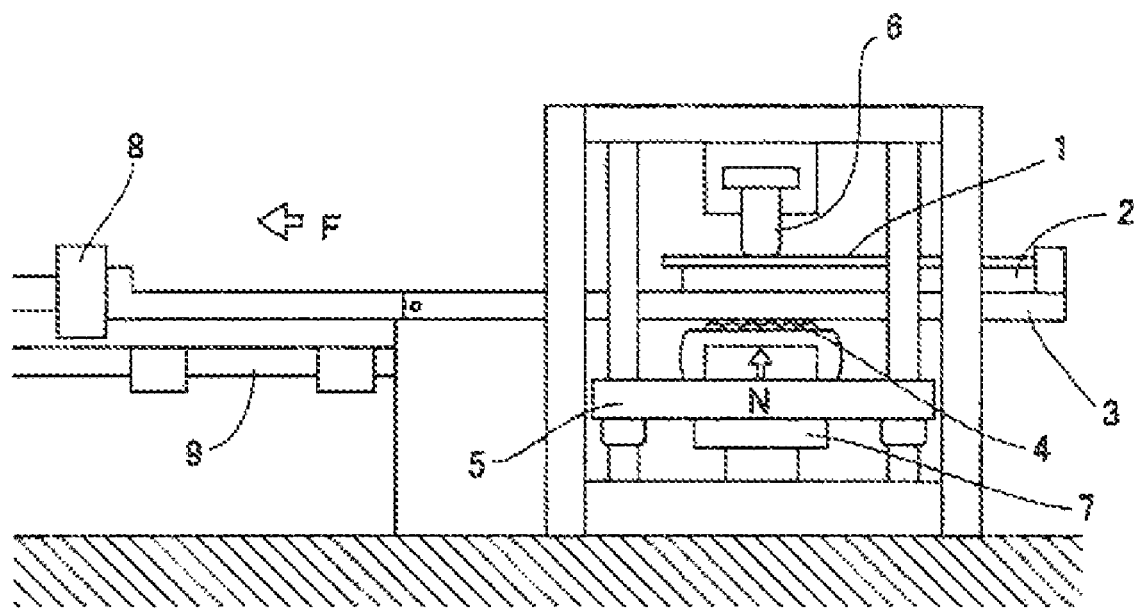
FIG. 1 is a schematic front view of an apparatus for measuring a coefficient of friction.

Reference numerals in the drawings represent the following:

| | |
|---|---|
| 1 | sample used for measuring coefficient of friction |
| 2 | sample stage |
| 3 | slide table |
| 4 | roller |
| 5 | slide-table support |
| 6 | bead |
| 7 | first load cell |
| 8 | second load cell |
| 9 | rail |
| N | pressing load |
| F | friction resistance |
| P | tensile load |

DETAILED DESCRIPTION

Our galvannealed steel sheets have an uneven surface due to the difference in reactivity at the interface between the steel sheet and a plating film. However, the planarization of a surface layer by a method such as skin pass rolling reduces irregularities of a plated surface. Thus, a force required to press projections on the plated surface with a die during press forming can be reduced to improve tribological properties.

A flat portion on a surface of a galvannealed steel sheet is a portion with which a die comes into direct contact during press forming. Thus, the presence of a hard and high-melting-point material that prevents adhesion to the die is important in improving tribological properties. Also in a hot-dip galvanized steel sheet and an electrogalvanized steel sheet which have surface irregularities smaller than those of the galvannealed steel sheet, each of their surfaces is naturally a portion with which a die comes into direct contact during press forming. Thus, the presence of a hard and high-melting-point material in their surface layers is important for improving tribological properties.

Also from this point of view, the formation of an oxide layer on a surface layer is effective in improving tribological properties. An oxide layer containing crystalline $3Zn(OH)_2 \cdot ZnSO_4 \cdot xH_2O$ is very effective. In particular, an oxide layer containing crystalline $3Zn(OH)_2 \cdot ZnSO_4 \cdot 3\text{-}5H_2O$ is significantly effective.

Whether crystalline $3Zn(OH)_2 \cdot ZnSO_4 \cdot 3\text{-}5H_2O$ is present in the oxide layer or not was determined by measuring an X-ray diffraction pattern of the oxide layer using X-ray diffractometry for a thin film and checking the resulting pattern against a standard pattern described in an ICDD card. The results demonstrated that peaks originating from oxides were observed at a diffraction angle ($2\theta$) of about 8° to about 12° and that these peaks were assigned to $3Zn(OH)_2 \cdot ZnSO_4 \cdot 3H_2O$ (ICDD card: 39-689), $3Zn(OH)_2 \cdot ZnSO_4 \cdot 4H_2O$ (ICDD card: 44-673), and $3Zn(OH)_2 \cdot ZnSO_4 \cdot 5H_2O$ (ICDD card: 39-688), which are trihydrate, tetrahydrate, and pentahydrate, respectively.

A thickness of the oxide layer on the surface plating layer of 10 nm or more results in a zinc-based metal plated steel sheet having good tribological properties. A thickness of 20 nm or more is more effective. This is because the oxide layer remains even if the oxide layer on the surface layer is worn in press forming in which the contact area between a die and a workpiece is large, thus not leading to a reduction in tribological properties. On the other hand, the upper limit of the thickness is not set. A thickness exceeding 200 nm results in a reduction in etch rate with a chemical conversion treatment liquid even when the oxide layer has Zn—OH bonds, thus leading to difficulty in the formation of a dense, uniform chemical conversion film. The thickness is therefore desirably 200 nm or less.

The most effective method for forming an oxide layer containing crystalline $3Zn(OH)_2 \cdot ZnSO_4 \cdot 3\text{-}5H_2O$ on a surface of a zinc-based metal plated steel sheet uses a reaction with an aqueous solution. In particular, a liquid film of a solution containing Zn ions and sulfate ions is formed on a surface of a steel sheet and allowed to stand for a predetermined time, thereby forming the oxide layer containing crystalline $3Zn(OH)_2 \cdot ZnSO_4 \cdot 3\text{-}5H_2O$ on the surface. In the case of using a solution containing only Zn ions, crystalline $3Zn(OH)_2 \cdot ZnSO_4 \cdot 3\text{-}5H_2O$ is not formed. In the case of using the solution containing Zn ions and sulfate ions, a higher sulfate ion concentration results in a tendency to promote the formation of crystalline $3Zn(OH)_2 \cdot ZnSO_4 \cdot 3\text{-}5H_2O$. Furthermore, higher concentrations of Zn ions and sulfate ions results in a tendency to form an oxide film having a larger thickness.

The coating weight of a zinc-based metal plated steel sheet including an oxide layer on a surface of the sheet is preferably in the range of 20 to 150 g/m² per surface. The reason for this is as follows: At an amount of the plating film of less than 20 g/m², the steel sheet has low resistance to corrosion because of a small amount of the plating film. An amount of the plating film exceeding 150 g/m² results in sufficient resistance to corrosion but may cause peeling of the plating film during processing. In particular, with respect to a galvannealed steel sheet, when galvannealing is performed in such a manner that good weldability and paintability, which are features of the galvannealed steel sheet, are satisfied, the formation of a Γ phase cannot be avoided at the interface between the plating film and the steel sheet, causing peeling of the plating film, e.g., powdering.

The Fe concentration in the plating film of the galvannealed steel sheet is preferably in the range of 6% to 14% by mass. The reason for this is as follows: At an Fe concentration of less than 6% by mass, a pure Zn phase (η phase) remains on the surface, so that the weldability, the paintability, and the like cannot be satisfied. On the other hand, an Fe concentration exceeding 14% by mass results in the formation of a thick Γ phase at the interface between the plating film and the steel sheet, thereby reducing adhesion of the plating film. To control the Fe concentration within the range, it is important to allow a plating bath to contain an appropriate amount of Al. The Al concentration needs to be in the range of 0.05% to 0.40% by mass.

For a hot-dip galvanized steel sheet, it is important that a plating bath contain Al in an appropriate amount in order that a thick alloy layer is not formed at the interface between the plating film and the steel sheet. The Al concentration needs to be in the range of 0.15% to 0.40% by mass.

The proportion of the area of a flat portion with respect to a plated surface is desirably in the range of 20% to 80%. At less than 20%, the contact area between a die and a portion (recessed portion) except for the flat portion is increased. With respect to the area of a portion in actual contact with the die, the proportion of the area of the flat portion where an oxide thickness can be assuredly controlled is reduced, thus reducing the effect of improving press formability. The portion except for the flat portion serves to hold press oil during press forming. Thus, when the proportion of the area of the portion except for the flat portion is less than 20% (when the proportion of the area of the flat portion exceeds 80%), the lack of oil can easily occur during press forming, so that the effect of improving press formability is reduced.

In the case of producing a galvannealed steel sheet or hot-dip galvanized steel sheet, a plating bath needs to contain Al. However, additive element components other than Al are not particularly limited. That is, even if Pb, Sb, Si, Sn, Mg, Mn, Ni, Ti, Li, Cu, and other elements are contained or added in addition to Al, the effect is not impaired.

In the case of producing an electrogalvanized steel sheet, a plating bath may mainly contain zinc. The plating bath may contain other metals and oxides as long as the effect is not impaired.

In a zinc-based metal plated steel sheet, the use of a high-tensile steel sheet as an underlying steel sheet provides an effect such as a reduction in weight and is thus preferred. For example, a concept regarding a reduction in the weight of an automobile body is that the use of the high-tensile steel sheet can reduce the weight of components (reduction in thickness of the sheet) while the crash performance of the body is maintained. In general, however, press formability tends to decrease as increasing tensile strength. The high-tensile steel sheet apparently has inferior press formability. We conducted intensive studies to improve the press formability of a high-tensile steel sheet and have found that the formation of an oxide layer containing crystalline $3Zn(OH)_2 \cdot ZnSO_4 \cdot 3-5H_2O$ on a surface layer extremely improves the press formability of the high-tensile steel sheet. This enables the high-tensile steel sheet to be applied to applications in which the use of the high-tensile steel sheet is difficult from the viewpoint of formability, thus achieving the effect of the reduction in weight described above. The type of steel sheet is not particularly limited. To sufficiently provide the effect of the reduction in weight, application to a high-tensile steel sheet having a tensile strength of 340 MPa or more is preferred.

Our steel sheets and methods will be described in further detail by examples.

EXAMPLES

Example 1

A plating film having a coating weight of 60 g/m$^2$, an Fe concentration of 10% by mass, and an Al concentration of 0.20% by mass was formed by a common galvannealing process on a cold-rolled steel sheet having a thickness of 0.8 mm. Then the steel sheet was subjected to skin pass rolling. In this case, the proportion of the area of a flat portion varied slightly with sampling positions but was in the range of 40% to 60%.

Oxidation treatment was performed as follows: The galvannealed steel sheet was immersed in an aqueous solution containing zinc sulfate heptahydrate. The amount of a liquid film attached on a surface was controlled with a rubber roll so as to be 10 g/m$^2$. The resulting steel sheet was allowed to stand in air for 10 to 60 seconds, washed with water, and dried. For comparison purposes, an aqueous solution containing zinc nitrate hexahydrate and an acidic solution containing sodium acetate and ferrous sulfate were used. The temperature of all solutions used for the treatment was set to 35° C.

Furthermore, a hot-dip galvanized steel sheet and an electrogalvanized steel sheet that have a thickness of 0.8 mm were prepared. A plating film having a coating weight of 70 g/m$^2$ was formed by a common hot-dip galvanizing process on the hot-dip galvanized steel sheet. The resulting steel sheet was subjected to skin pass rolling. A plating film having a coating weight of 50 g/m$^2$ was formed by a common electrogalvanizing process on the electrogalvanized steel sheet.

Oxidation treatment was performed as follows: Each of the hot-dip galvanized steel sheet and the electrogalvanized steel sheet was immersed in an aqueous solution containing zinc sulfate heptahydrate. The amount of a liquid film attached on a surface was controlled with a rubber roll so as to be 10 g/m$^2$. The resulting steel sheet was allowed to stand in air for 10 to 60 seconds, washed with water, and dried. The temperature of all solutions used for the treatment was set to 35° C.

The measurement of coefficients of friction and measurement of thicknesses of oxide layers and analysis of $3Zn(OH)_2 \cdot ZnSO_4 \cdot 3-5H_2O$ of the oxidation-treated plated steel sheets were performed as follows. For comparison purposes, steel sheets that were not subjected to oxidation treatment were also studied in the same way as above.

(1) Test for Evaluating Press Formability (Test for Measuring Coefficient of Friction)

To evaluate press formability, coefficient of friction of each of the samples was measured. FIG. 1 is a schematic front view of an apparatus for measuring a coefficient of friction. As shown in the figure, a sample 1, taken from the steel sheet, used for measuring a coefficient of friction was fixed to a sample stage 2. The sample stage 2 was fixed to an upper surface of a slide table 3 that was movable horizontally. A slide-table support 5 that was movable vertically was provided and had rollers 4 in contact with a lower surface of the slide table 3. By raising the slide-table support 5, a bead 6 imposed a pressing load N on the sample 1 for measuring a coefficient of friction. A first load cell 7 for measuring the pressing load N was attached to the slide-table support 5. A second load cell 8 for measuring a friction resistance F that allowed the slide table 3 to move horizontally while the pressing load was being imposed on the sample was attached to an end of the slide table 3. As lubricant oil, wash oil for press, Preton (registered trademark) R352L manufactured by Sugimura Chemical Industrial Co., Ltd. was applied to surfaces of the sample 1, and then the test was performed.

Figure 2:
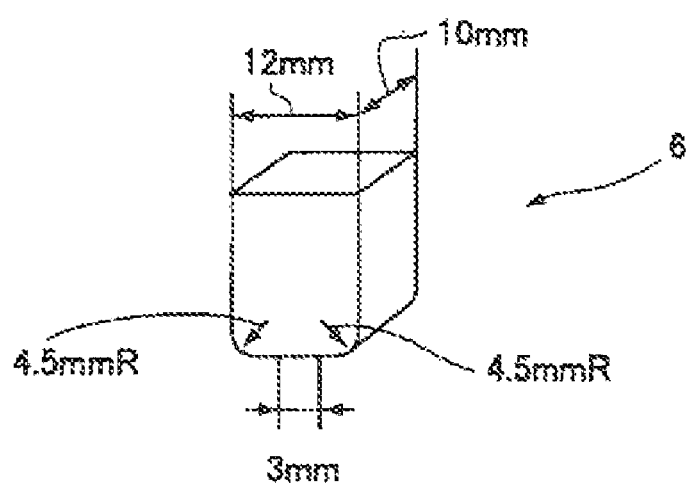
FIG. 2 is a schematic perspective view of the shape and dimensions of a bead shown in FIG. 1.

FIG. 2 is a schematic perspective view of the shape and dimensions of the bead used. Sliding was performed while the undersurface of the bead 6 is pressed against a surface of the sample 1. With respect to the shape of the bead 6 shown in FIG. 2, the width was 10 mm, and the length in the sliding direction of the sample was 12 mm. Lower ends in the sliding direction were in the form of curved surfaces each having a curvature of 4.5 mmR. The undersurface of the bead against which the sample was pressed was in the form of a plane with a width of 10 mm and a length in the sliding direction of 3 mm.

The test for measuring a coefficient of friction was performed under two conditions described below.

Condition 1

The bead shown in FIG. 2 was used. The pressing load N was set to 400 kgf. The speed of movement of each sample (the speed of horizontal movement of the slide table 3) was set to 100 cm/min.

Condition 2

The bead shown in FIG. 2 was used. The pressing load N was set to 400 kgf. The speed of movement of the sample (the speed of horizontal movement of the slide table 3) was set to 20 cm/min.

Coefficients μ of friction between the samples and the bead were calculated using the following formula: μ=F/N.

(2) Measurement of Thickness of Oxide Layer

Measurement of the thickness of each oxide layer was performed with an X-ray fluorescence analyzer. A voltage and a current applied to a tube during measurement were 30 kV and 100 mA, respectively. An analyzing crystal was set to TAP to detect the O-Kα ray. In the case of the measurement of the O-Kα ray, intensities at the background in addition to the peak position were measured to calculate the net intensity of the O-Kα ray. An integral time at each of the peak position and the background was set to 20 seconds.

Silicon wafer pieces formed by cleavage and including silicon oxide films having a thickness of 96 nm, 54 nm, and 24 nm were placed on the sample stage together with the samples to calculate the intensity of the O-Kα ray on the basis of the silicon oxide films. A calibration curve showing the relationship between the thickness of the oxide film and the intensity of the O-Kα ray was formed on the basis of the data. The thickness of the oxide layer of each sample was calculated in terms of the thickness of the silicon oxide film.

(3) Determination of Presence of Crystalline $3Zn(OH)_2 \cdot ZnSO_4 \cdot 3\text{-}5H_2O$ The presence of crystalline $3Zn(OH)_2 \cdot ZnSO_4 \cdot 3\text{-}5H_2O$ was determined by an X-ray diffractometry for a thin film. An X-ray diffraction pattern was measured by a thin-film method using the Cu-Kα ray at an incident angle of 0.5°. A diffraction peak corresponding to a crystal structure of $3Zn(OH)_2 \cdot ZnSO_4 \cdot 3\text{-}5H_2O$ was observed at a diffraction angle (2θ) of about 8° to about 12°.

For the galvannealed steel sheet, the presence of crystalline $3Zn(OH)_2 \cdot ZnSO_4 \cdot 3\text{-}5H_2O$ was determined on the basis of the intensity ratio of the diffraction peak to a diffraction peak that was observed at about 42° and that originated from an alloy layer of iron and zinc. It was determined that a film containing crystalline $3Zn(OH)_2 \cdot ZnSO_4 \cdot 3\text{-}5H_2O$ was formed when a peak intensity ratio, i.e., (peak intensity of $3Zn(OH)_2 \cdot ZnSO_4 \cdot 3\text{-}5H_2O$)/(peak intensity of the alloy of iron and zinc), of 0.020 or more was obtained, wherein the peak intensities calculated by subtracting their respective backgrounds were used.

For each of the hot-dip galvanized steel sheet and the electrogalvanized steel sheet, the presence of crystalline $3Zn(OH)_2 \cdot ZnSO_4 \cdot 3\text{-}5H_2O$ was determined on the basis of the intensity ratio of a diffraction peak that corresponded to a crystal structure of $3Zn(OH)_2 \cdot ZnSO_4 \cdot 3\text{-}5H_2O$ and that was observed at a diffraction angle (2θ) of about 8° to about 12° to a diffraction peak that was observed at about 36° and that originated from a zinc η layer. It was determined that a film containing crystalline $3Zn(OH)_2 \cdot ZnSO_4 \cdot 3\text{-}5H_2O$ was formed when a peak intensity ratio, i.e., (peak intensity of $3Zn(OH)_2 \cdot ZnSO_4 \cdot 3\text{-}5H_2O$)/(peak intensity of the zinc η layer), of 0.020 or more was obtained, wherein the peak intensities calculated by subtracting their respective backgrounds were used.

The peaks observed at a diffraction angle (2θ) of about 8° to about 12° were assigned to $3Zn(OH)_2 \cdot ZnSO_4 \cdot 3H_2O$ (ICDD card: 39-689), $3Zn(OH)_2 \cdot ZnSO_4 \cdot 4H_2O$ (ICDD card: 44-673), and $3Zn(OH)_2 \cdot ZnSO_4 \cdot 5H_2O$ (ICDD card: 39-688), which are trihydrate, tetrahydrate, and pentahydrate, respectively.

Table 1 shows conditions of the oxidation treatment for the galvannealed steel sheet and the results. Table 2 shows conditions of the oxidation treatment for the hot-dip galvanized steel sheet and the electrogalvanized steel sheet and the results.

TABLE 1

| No. | Solution used | pH of solution | Time until washing with water (s) | Thickness of oxide film (nm) | Coefficient of friction Condition 1 | Coefficient of friction Condition 2 | Peak intensity ratio *) | Remarks |
|---|---|---|---|---|---|---|---|---|
| 1 | — | — | — | 9 | 0.175 | 0.256 | — | Comparative Example 1 |
| 2 | Zinc sulfate heptahydrate | 5.5 | 10 s | 28 | 0.133 | 0.169 | 0.025 | Inventive Example 1 |
| 3 | 20 g/l | | 30 s | 34 | 0.134 | 0.163 | 0.049 | Inventive Example 2 |
| 4 | | | 60 s | 45 | 0.132 | 0.163 | 0.080 | Inventive Example 3 |
| 5 | Zinc sulfate heptahydrate | 5.2 | 10 s | 30 | 0.130 | 0.168 | 0.031 | Inventive Example 4 |
| 6 | 50 g/l | | 30 s | 36 | 0.129 | 0.166 | 0.054 | Inventive Example 5 |
| 7 | | | 60 s | 52 | 0.126 | 0.158 | 0.107 | Inventive Example 6 |
| 8 | Zinc nitrate hexahydrate | 5.6 | 10 s | 22 | 0.160 | 0.228 | — | Comparative Example 2 |
| 9 | 20 g/L | | 30 s | 28 | 0.159 | 0.220 | 0.008 | Comparative Example 3 |
| 10 | | | 60 s | 31 | 0.155 | 0.215 | 0.011 | Comparative Example 4 |
| 11 | Zinc nitrate hexahydrate | 5.2 | 10 s | 24 | 0.158 | 0.225 | 0.012 | Comparative Example 5 |
| 12 | 50 g/L | | 30 s | 32 | 0.159 | 0.218 | 0.010 | Comparative Example 6 |
| 13 | | | 60 s | 40 | 0.155 | 0.220 | 0.013 | Comparative Example 7 |
| 14 | Sodium acetate | 2.0 | 10 s | 18 | 0.153 | 0.181 | — | Comparative Example 8 |
| 15 | Ferrous sulfate | (pH was adjusted to | 30 s | 24 | 0.152 | 0.175 | 0.006 | Comparative Example 8 |
| 16 | 40 g/L each | 2.0 with sulfuric acid) | 60 s | 35 | 0.148 | 0.177 | 0.017 | Comparative Example 9 |

*) No peak was observed at 8° to 12°.

TABLE 2

| No. | Sample *1) | Solution used | pH of solution | Time until washing with water (s) | Thickness of oxide film (nm) | Coefficient of friction Condition 1 | Coefficient of friction Condition 2 | Peak intensity ratio *2) |
|---|---|---|---|---|---|---|---|---|
| 17 | GI | — | — | — | 6 | 0.135 | 0.286 | — |
| 18 | | Zinc sulfate heptahydrate | 5.2 | 10 s | 25 | 0.135 | 0.162 | 0.022 |
| 19 | | 50 g/l | | 30 s | 35 | 0.128 | 0.160 | 0.041 |
| 20 | | | | 60 s | 44 | 0.125 | 0.158 | 0.080 |
| 21 | EG | — | — | — | 9 | 0.146 | 0.286 | — |
| 22 | | Zinc sulfate heptahydrate | 5.2 | 10 s | 27 | 0.135 | 0.169 | 0.024 |
| 23 | | 50 g/L | | 30 s | 34 | 0.131 | 0.168 | 0.043 |
| 24 | | | | 60 s | 43 | 0.129 | 0.160 | 0.075 |

*1) GI: hot-dip galvanized steel sheet, EG: electrogalvanized steel sheet
*2) No peak was observed at 8° to 12°.

The results from Tables 1 and 2 show the following.

In each of Nos. 1, 17, and 21, which were not subjected to oxidation treatment, the oxide layer had a thickness of less than 10 nm. An oxide film adequate to improve tribological properties was not formed on a flat portion, thus leading to a high coefficient of friction.

In each of Nos. 2 to 7, 18 to 20, and 22 to 24, the peak intensity ratio was 0.020 or more. The oxide layer containing crystalline $3Zn(OH)_2 \cdot ZnSO_4 \cdot 3\text{-}5H_2O$ was formed and had a thickness of 10 nm or more, so that the coefficient of friction was stabilized at a low level, thus sufficiently improving tribological properties.

In each of Nos. 8 to 16, although the oxide layer having a thickness of 10 nm or more was formed on a flat portion, the peak intensity ratio was less than 0.020. Crystalline $3Zn(OH)_2 \cdot ZnSO_4 \cdot 3\text{-}5H_2O$ was not formed. A high coefficient of friction was measured. The effect of sufficiently improving tribological properties was not provided.

Example 2

Galvannealed steel sheets having different strength levels and each having a thickness of 1.2 mm were used. Oxidation treatment was performed as follows: Each of the galvannealed steel sheets was immersed in an aqueous solution (pH: 5.5, temperature: 35° C.) containing zinc sulfate heptahydrate (concentration: 20 g/L). The amount of a liquid film attached on a surface was controlled with a rubber roll so as to be 10 g/m². The resulting steel sheet was allowed to stand in air for 10 to 60 seconds, washed with water, and dried. Galvannealing was performed by a common alloying treatment to form a plating film having a coating weight of 45 to 50 g/m² and an Fe concentration of 10% to 11% by mass. Then skin pass rolling was performed in such a manner that the proportion of the area of a flat portion was in the range of 40% to 60%.

The measurement of thicknesses of oxide layers and analysis of $3Zn(OH)_2 \cdot ZnSO_4 \cdot 3\text{-}5H_2O$ of the oxidation-treated galvannealed steel sheets were performed by the procedure described in Example 1. Furthermore, the measurement of mechanical properties and evaluation of press formability of the steel sheets were performed. Press formability was evaluated by a test for measuring a coefficient of friction and a stretch forming test. For comparison purposes, steel sheets that were not subjected to oxidation treatment were also studied in the same way as above.

(1) Measurement of Mechanical Property

A tensile test was performed in compliance with JIS Z2241 using No. 5 test pieces according to JIS Z2201, a longitudinal direction (tensile direction) of each of the test pieces being defined as a direction perpendicular to the rolling direction.

(2) Test for Evaluating Press Formability (Test for Measuring Coefficient of Friction)

Coefficients of friction of samples were measured by the procedure described in Example 1 under conditions 3.

Condition 3

Figure 3:
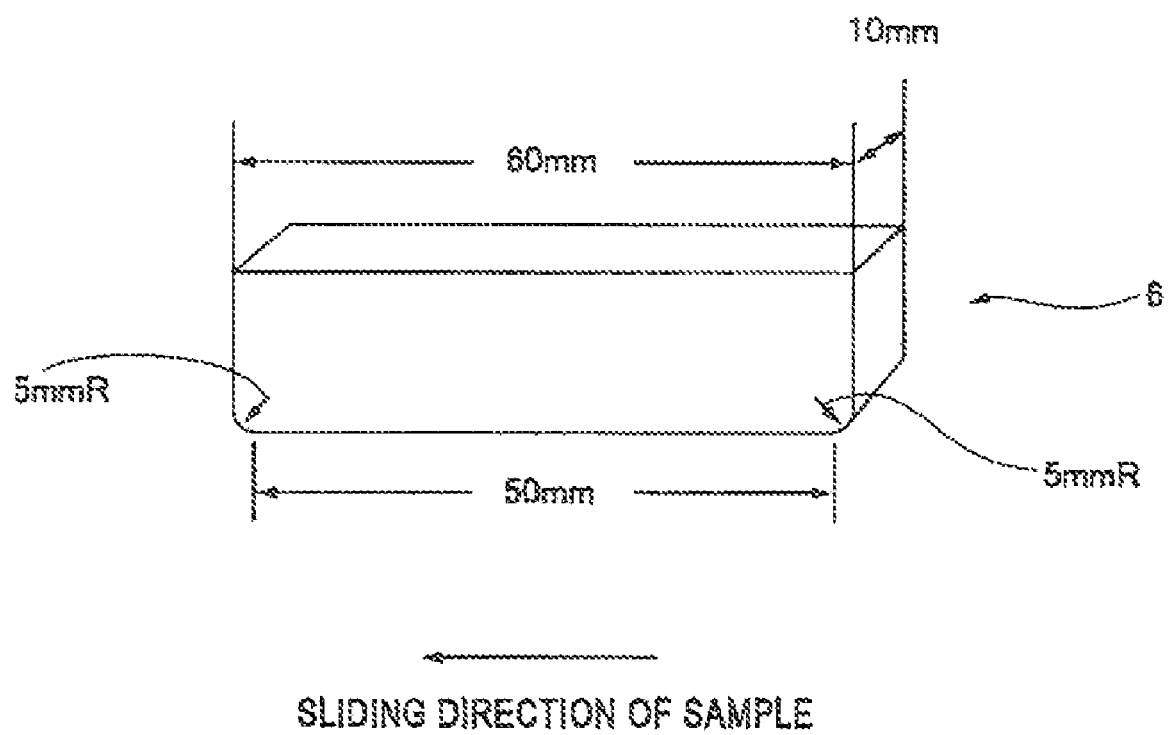
FIG. 3 is a schematic perspective view of the shape and dimensions of a bead shown in FIG. 1.

The bead shown in FIG. 3 was used. The pressing load N was set to 400 kgf. The speed of movement of each sample (the speed of horizontal movement of the slide table 3) was set to 120 cm/min. Coefficients μ of friction between the samples and the bead were calculated using the following formula: μ=F/N.

(3) Test for Evaluating Press Formability (Stretch Forming Test)

A spherical stretch forming test of each sample having a size of 200 mm×200 mm was performed with a punch having a diameter of 150 mm (diameter of a die: 153 mm) to measure the maximum height of a formed portion when the rupture of the sample occurred. In this case, to suppress the feed of the sample, a fold pressure of 100 ton was applied. As lubricant oil, wash oil for press, Preton (registered trademark) R352L manufactured by Sugimura Chemical Industrial Co., Ltd. was applied to the sample.

Table 3 shows conditions of the oxidation treatment and the results.

TABLE 3

| No | Sample TS (MPa) | Sample YS (MPa) | Sample El (%) | Oxidation treatment | Time until washing with water (s) | Thickness of oxide film nm | Peak intensity ratio *) | Coefficient of friction Condition 3 | Stretch forming test Height of formed portion mm | Remarks |
|---|---|---|---|---|---|---|---|---|---|---|
| 1 | 350 | 240 | 42 | Performed | 10 | 32 | 0.025 | 0.160 | 45.6 | Inventive Example |
| 2 | 350 | 240 | 42 | Not performed | — | 6 | — | 0.225 | 40.1 | Comparative Example |
| 3 | 450 | 310 | 38 | Performed | 10 | 31 | 0.025 | 0.157 | 44.0 | Inventive Example |
| 4 | 450 | 310 | 38 | Not performed | — | 8 | — | 0.219 | 38.5 | Comparative Example |

TABLE 3-continued

| | Sample | | | | Time until washing with water (s) | Thickness of oxide film nm | Peak intensity ratio *) | Coefficient of friction Condition 3 | Stretch forming test Height of formed portion mm | |
|---|---|---|---|---|---|---|---|---|---|---|
| No | TS (MPa) | YS (MPa) | El (%) | Oxidation treatment | | | | | | Remarks |
| 5 | 620 | 390 | 29 | Performed | 10 | 30 | 0.022 | 0.156 | 41.1 | Inventive Example |
| 6 | 620 | 390 | 29 | Not performed | — | 6 | — | 0.224 | 35.5 | Comparative Example |
| 7 | 890 | 590 | 19 | Performed | 10 | 30 | 0.022 | 0.157 | 37.5 | Inventive Example |
| 8 | 890 | 590 | 19 | Not performed | — | 7 | — | 0.213 | 31.8 | Comparative Example |
| 9 | 1060 | 660 | 15 | Performed | 10 | 31 | 0.024 | 0.159 | 36.2 | Inventive Example |
| 10 | 1060 | 660 | 15 | Not performed | — | 7 | — | 0.225 | 30.5 | Comparative Example |
| 11 | 1500 | 800 | 13 | Performed | 10 | 30 | 0.022 | 0.155 | 35.3 | Inventive Example |
| 12 | 1500 | 800 | 13 | Not performed | — | 7 | — | 0.215 | 29.5 | Comparative Example |
| 13 | 2000 | 1100 | 10 | Performed | 10 | 31 | 0.022 | 0.156 | 34.4 | Inventive Example |
| 14 | 2000 | 1100 | 10 | Not performed | — | 8 | — | 0.210 | 28.6 | Comparative Example |

*) No peak was observed at 8° to 12°.

The results from Table 3 show the following.

In each of the samples that were not subjected to oxidation treatment (Comparative Examples: Nos. 2, 4, 6, 8, 10, 12, and 14), the oxide layer had a thickness of less than 10 nm. An oxide film adequate to improve tribological properties was not formed on a flat portion, thus leading to a high coefficient of friction.

In each of the samples that were subjected to oxidation treatment (Inventive Examples: Nos. 1, 3, 5, 7, 9, 11, and 13), the peak intensity ratio was 0.020 or more. The oxide layer containing crystalline $3Zn(OH)_2 \cdot ZnSO_4 \cdot 3\text{-}5H_2O$ was formed and had a thickness of 10 nm or more, so that the coefficient of friction was stabilized at a low level, thus sufficiently improving tribological properties.

Comparisons between the steel sheets having the same strength level (Nos. 1 and 2, Nos. 3 and 4, Nos. 5 and 6, Nos. 7 and 8, Nos. 9 and 10, Nos. 11 and 12, and Nos. 13 and 14) showed that heights of formed portions of samples that were subjected to oxidation treatment (Inventive Example) was higher than those of samples that were not subjected to oxidation treatment (Comparative Example) and that the samples that were subjected to oxidation treatment had sufficiently improved press formability.

INDUSTRIAL APPLICABILITY

The zinc-based metal plated steel sheet is excellent in tribological properties and press formability and can thus be applied in many fields, in particular, for automobile bodies.

The invention claimed is:

1. A galvannealed steel sheet comprising an oxide layer containing crystalline $3Zn(OH)_2 \cdot ZnSO_4 \cdot xH_2O$, wherein the oxide layer is located on a plated surface, the oxide layer has a thickness of 10 nm to 200 nm, the galvannealed steel sheet contains 6-14% by mass Fe and a proportion of an area of a flat portion with respect to the plated surface is 20% to 80%.

2. The galvannealed steel sheet according to claim 1, wherein the crystalline oxide layer is composed of $3Zn(OH)_2 \cdot ZnSO_4 \cdot 3\text{-}5H_2O$.

3. The galvannealed steel sheet according to claim 1, having a tensile strength of 340 MPa or more.

4. The galvannealed steel sheet according to claim 1, wherein the oxide layer consists essentially of crystalline $3Zn(OH)_2 \cdot ZnSO_4 \cdot xH_2O$.

* * * * *